(12) United States Patent
Neeff et al.

(10) Patent No.: US 7,968,728 B2
(45) Date of Patent: Jun. 28, 2011

(54) METHOD FOR PRODUCING CARBOXAMIDES

(75) Inventors: Arnd Neeff, Ennepetal (DE); Sergiy Pazenok, Solingen (DE)

(73) Assignee: Bayer Cropscience AG, Monheim (DE)

( * ) Notice: Subject to any disclaimer, the term of this patent is extended or adjusted under 35 U.S.C. 154(b) by 557 days.

(21) Appl. No.: 11/917,865

(22) PCT Filed: Jun. 7, 2006

(86) PCT No.: PCT/EP2006/005436
§ 371 (c)(1),
(2), (4) Date: Jun. 6, 2008

(87) PCT Pub. No.: WO2006/136288
PCT Pub. Date: Dec. 28, 2006

(65) Prior Publication Data
US 2009/0054661 A1    Feb. 26, 2009

(30) Foreign Application Priority Data

Jun. 18, 2005 (DE) .......................... 10 2005 028 294

(51) Int. Cl.
*C07D 231/16* (2006.01)

(52) U.S. Cl. .................................................. 548/374.1
(58) Field of Classification Search .................. None
See application file for complete search history.

(56) References Cited

U.S. PATENT DOCUMENTS 7,396,939 B2 *   7/2008   Schmitt et al. ............. 548/369.4

FOREIGN PATENT DOCUMENTS

EP          0 776 889          6/1997

OTHER PUBLICATIONS

Lalonde et al., "Triamides Prepared by the Diacylation of Amides", Journal of Organic Chemistry, vol. 35, No. 3, 1970, pp. 771-774.
International Search Report No. PCT/EP2006/005436, dated Aug. 18, 2006, 4 pgs.

* cited by examiner

*Primary Examiner* — Kamal Saeed
(74) *Attorney, Agent, or Firm* — Baker Donelson Bearman, Caldwell & Berkowitz, PC

(57) ABSTRACT

The present invention relates to a novel process for preparing known fungicidally active 1,3-dimethyl-5-fluoro-1H-pyrazole-4-carboxamides from the corresponding acid fluoride and aniline derivatives in the presence of alkylpyridine derivatives as an acid acceptor.

11 Claims, No Drawings

METHOD FOR PRODUCING CARBOXAMIDES

CROSS-REFERENCE TO RELATED APPLICATIONS

The present application is a 371 of application Serial No. PCT/EP2006/005436, filed Jun. 7, 2006, which claims priority under 35 U.S.C. §119 to German application no. DE 10 2005 028 294.6, filed Jun. 18, 2005, the content of which is incorporated herein by reference in its entirety.

BACKGROUND OF INVENTION

1. Field of Invention

The present invention relates to a novel process for preparing known fungicidally active 1,3-dimethyl-5-fluoro-4-carboxamides from the corresponding acid fluoride and aniline derivatives in the presence of alkylpyridine derivatives as an acid acceptor.

2. Description of Related Art

It is already known that 1,3-dimethyl-5-fluoro-1H-pyrazole-4-carboxamides are obtained by reacting the corresponding acid fluoride with the desired aniline derivative (cf. EP-A 0 776 889). According to this description, preference is given to using bicyclic tertiary amines such as diazabicyclooctane (DABCO), diazabicyclononene (DBN) or diazabicycloundecene (DBU) as the acid acceptor. The reaction with DABCO only affords a yield of 80%. Moreover, DABCO is unsuitable for industrial scale reactions, since this reagent is very expensive and cannot be recycled.

SUMMARY OF INVENTION

It has now been found that carboxamides of the formula (I)

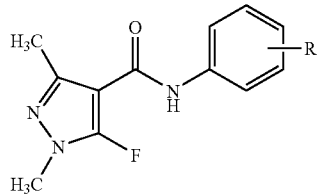

(I)

in which
R is $C_3$-$C_{12}$-cycloalkyl, $C_3$-$C_{12}$-cycloalkenyl, $C_6$-$C_{12}$-bicycloalkyl, $C_2$-$C_{12}$-oxacycloalkyl, $C_4$-$C_{12}$-oxacycloalkenyl, $C_3$-$C_{12}$-thiacycloalkyl, $C_4$-$C_{12}$-thiacycloalkenyl, $C_2$-$C_{12}$-azacycloalkyl, each of which may optionally be mono- or polysubstituted identically or differently by $C_1$-$C_8$-alkyl, $C_1$-$C_8$-alkoxy, halogen and/or cyano, or phenyl which is optionally mono- to pentasubstituted identically or differently, where the substituents are each selected from the list $W^1$,
or unsubstituted $C_2$-$C_{20}$-alkyl,
or $C_1$-$C_{20}$-alkyl which is mono- or polysubstituted identically or differently by halogen, $C_1$-$C_6$-alkylthio, $C_1$-$C_6$-alkylsulfinyl, $C_1$-$C_6$-alkylsulfonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulfinyl, $C_1$-$C_6$-haloalkylsulfonyl, $C_1$-$C_6$-haloalkoxy, $C_1$-$C_6$-haloalkylamino, halo-di($C_1$-$C_6$-alkyl)amino, —$SiR^1R^2R^3$ and/or $C_3$-$C_6$-cycloalkyl, where the cycloalkyl moiety may in turn optionally be mono- to tetrasubstituted identically or differently by halogen, $C_1$-$C_{20}$-alkyl and/or $C_1$-$C_4$-haloalkyl,
$W^1$ is halogen, cyano, nitro, amino, hydroxyl, $C_1$-$C_8$-alkyl, $C_1$-$C_8$-alkoxy, $C_1$-$C_8$-alkylthio, $C_1$-$C_8$-alkylsulfinyl, $C_1$-$C_8$-alkylsulfonyl, $C_2$-$C_6$-alkenyl, $C_2$-$C_6$-alkenyloxy; $C_1$-$C_6$-haloalkyl, $C_1$-$C_6$-haloalkoxy, $C_1$-$C_6$-haloalkylthio, $C_1$-$C_6$-haloalkylsulfinyl or $C_1$-$C_6$-haloalkylsulfonyl having in each case from 1 to 13 identical or different halogen atoms; $C_2$-$C_6$-haloalkenyl or $C_2$-$C_6$-haloalkenyloxy having in each case from 1 to 11 identical or different halogen atoms; $C_3$-$C_6$-cycloalkyl or $C_3$-$C_6$-cycloalkyloxy;
$R^1$ and $R^2$ are each independently hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl,
$R^3$ is hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or in each case optionally substituted phenol or phenylalkyl,
are obtained in a simple manner by
reacting 5-fluoro-1,3-dimethyl-1H-pyrazole-4-carbonyl fluoride of the formula (II)

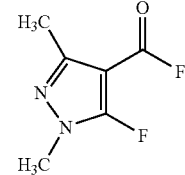

(II)

with aniline derivatives of the formula (III)

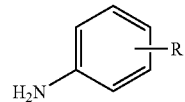

(III)

in which R is as defined above,
in the presence of an acid acceptor of the formula (IV)

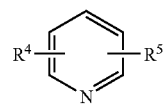

(IV)

in which $R^4$ and $R^5$ are each independently hydrogen or $C_1$-$C_3$-alkyl.

DETAILED DESCRIPTION OF A PREFERRED EMBODIMENT

It is surprisingly possible to prepare the carboxamides of the formula (I) under the inventive conditions in high purity and selectivity with good yields through the selection of the acid acceptor of the formula (IV). A further advantage of the process according to the invention is that the acid acceptor of the formula (IV) used can be recovered completely.

When, for example, 5-fluoro-1,3-dimethyl-1H-pyrazole-4-carbonyl fluoride and 2-(1,3-dimethylbutyl)phenylamine are used as starting materials, and 2,6-dimethylpyridine is used as the acid acceptor, the process according to the invention can be illustrated by the following scheme:

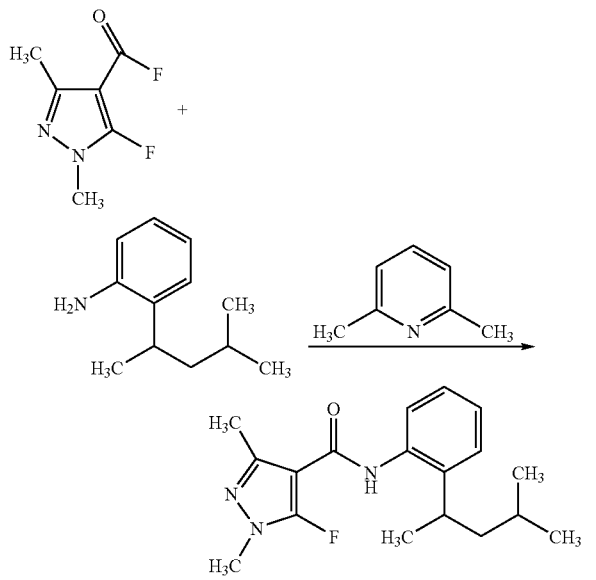

The 5-fluoro-1,3-dimethyl-1H-pyrazole-4-carbonyl fluoride of the formula (II) used as a starting material in the performance of the process according to the invention is known (cf. EP-A 0 776 889).

The aniline derivatives also used as starting materials in the performance of the process according to the invention are defined in general terms by the formula (III).

R is preferably $C_3$-$C_8$-cycloalkyl, $C_3$-$C_8$-cycloalkenyl, $C_6$-$C_{10}$-bicycloalkyl, $C_2$-$C_7$-oxacycloalkyl, $C_4$-$C_7$-oxacycloalkenyl, $C_3$-$C_7$-thiacycloalkyl, $C_4$-$C_7$-thiacycloalkenyl, $C_2$-$C_7$-azacycloalkyl, each of which may optionally be mono- to tetrasubstituted identically or differently by $C_1$-$C_4$-alkyl, $C_1$-$C_4$-alkoxy, fluorine, chlorine, bromine and/or cyano, or phenyl which is mono- to trisubstituted identically or differently, where the substituents are selected from the list $W^1$, or unsubstituted $C_2$-$C_{12}$-alkyl (such as ethyl and straight-chain or branched propyl, butyl, pentyl, hexyl, heptyl, octyl, nonyl, decyl, undecyl and dodecyl)

or $C_1$-$C_{12}$-alkyl (such as methyl, ethyl and straight-chain or branched propyl, butyl, pentyl, hexyl, heptyl, octyl, nonyl, decyl, undecyl and dodecyl) which is mono- or polysubstituted identically or differently by fluorine, chlorine, bromine, iodine, $C_1$-$C_6$-alkylthio, $C_1$-$C_4$-alkylsulfinyl, $C_1$-$C_4$-alkylsulfonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulfinyl, $C_1$-$C_4$-haloalkylsulfonyl, $C_1$-$C_4$-haloalkoxy, $C_1$-$C_4$-haloalkylamino, halo-di($C_1$-$C_4$-alkyl)amino having in each case from 1 to 9 fluorine, chlorine and/or bromine atoms, —$SiR^1R^2R^3$, cyclopropyl, dichlorocyclopropyl, cyclobutyl, cyclopentyl or cyclohexyl.

R is more preferably cyclopentyl, cyclohexyl, cycloheptyl, bicyclo[2.2.1]heptyl, or phenyl monosubstituted in the 4 position, phenyl disubstituted identically or differently in the 3,4, 2,3, 2, 4 or 3,5 position, or phenyl trisubstituted identically or differently in the 2,4,6 position, where the substituents are each selected from the list $W^1$, or unsubstituted $C_3$-$C_{10}$-alkyl (such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl)

or $C_1$-$C_{10}$-alkyl (such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl) which is mono- or polysubstituted identically or differently by fluorine, chlorine, methylthio, ethylthio, n- or isopropylthio, n-, iso-, sec-, tert-butylthio, pentylthio, hexylthio, methylsulfonyl, ethylsulfonyl, n- or isopropylsulfonyl, n-, iso-, sec-, tert-butylsulfonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylthio, trifluoromethoxy, —$SiR^1R^2R^3$, cyclopropyl, dichlorocyclopropyl, cyclobutyl, cyclopentyl or cyclohexyl.

$W^1$ is preferably fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy.

$W^1$ is more preferably fluorine, chlorine or bromine.

$R^1$ and $R^2$ are each independently preferably $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^1$ and $R^2$ are each independently more preferably methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^1$ and $R^2$ are each independently most preferably methyl, methoxy, methoxymethyl or methylthiomethyl.

$R^1$ and $R^2$ are especially preferably each methyl.

$R^3$ is preferably $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^3$ is more preferably methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^3$ is most preferably methyl, ethyl, n- or isopropyl, iso- or tert-butyl, methoxy, isopropoxy, iso- or tert-butoxy.

$R^3$ is especially preferably methyl.

Preference is given to using aniline derivatives of the formula (III-1)

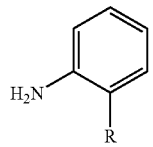

in which R is as defined above
in the process according to the invention.

Preference is also given to using aniline derivatives of the formula (III-2)

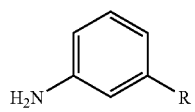

in which R is as defined above
in the process according to the invention.

Preference is also given to using aniline derivatives of the formula (III-3)

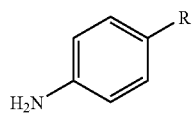

in which R is as defined above
in the process according to the invention.

Particular preference is given to using aniline derivatives of the formula (III-1).

Aniline derivatives of the formula (III) or (III-1), (III-2) and (III-3) are known or can be prepared in a known manner (cf. EP-A 0 776 889, WO 03/010149).

The acid acceptors used in the performance of the process according to the invention are defined in general terms by the formula (IV). In this formula (IV), $R^4$ and $R^5$ are preferably each independently methyl or ethyl. Particular preference is given to the following acid acceptors of the formula (IV): 2-methylpyridine, 2,3-dimethylpyridine, 2-methyl-5-ethylpyridine, 2,6-dimethylpyridine, 2,4-dimethylpyridine, 3,4-dimethylpyridine, 2,4,6-trimethylpyridine.

Acid acceptors of the formula (IV) are known synthesis chemicals.

The process according to the invention can be performed in the presence of a diluent. Useful diluents for this purpose are all inert organic solvents, preferably aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoramide, more preferably chlorobenzene or toluene.

In the performance of the process according to the invention, the reaction temperatures can be varied within a wide range. In general, temperatures of 100° C. to 150° C., preferably temperatures of 120° C. to 145° C., are employed.

In the performance of the process according to the invention, generally between 0.8 and 1.5 mol, preferably equimolar amounts, of aniline derivatives of the formula (III) and between 0.8 and 1.5 mol, preferably equimolar amounts, of an acid acceptor of the formula (IV) are used per mole of the 5-fluoro-1,3-dimethyl-1H-pyrazole-4-carbonyl fluoride of the formula (II).

Depending on the reactivity of the reactants, the reaction time may be up to 30 hours, but the reaction can also be terminated earlier in the case of complete conversion. Preference is given to reaction times of from 10 to 20 hours.

All processes according to the invention are generally performed under standard pressure. However, it is also possible to work under elevated or reduced pressure—generally between 0.1 bar and 10 bar.

The carboxamides of the formula (I) preparable by the process according to the invention are valuable fungicides (cf., for example, WO 03/010149).

The inventive preparation of carboxamides of the formula (I) is described in the examples which follow, which further illustrate the above description. However, the examples should not be interpreted in a restrictive manner.

PREPARATION EXAMPLES

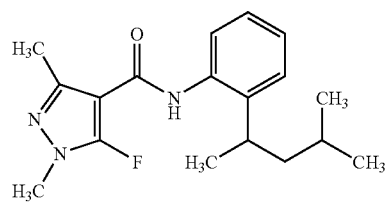

Under protective gas (argon), a solution of 11.25 g (105 mmol) of 2,6-dimethylpyridine and 18.05 g (100 mmol) of 2-(1,3-dimethylbutyl)phenylamine in 40 ml of chlorobenzene is initially charged. 16.17 g (100 mmol) of 5-fluoro-1, 3-dimethyl-1H-pyrazole-4-carbonyl fluoride are added and the mixture is stirred under reflux for 21 h. For workup, the mixture is allowed to cool, stirred with 100 ml of 1 N hydrochloric acid and extracted three times with 100 ml each time of ethyl acetate. The combined organic phases are washed once with 100 ml of water, dried over magnesium sulfate and concentrated under reduced pressure. The resulting suspension is stirred with 50 ml of hexane at room temperature for 2 h. This affords 28.25 g (88% of theory) of N-[2-(1,3-dimethylbutyl)phenyl]-5-fluoro-1,3-dimethyl-1H-pyrazole-4-carboxamide in the form of crystals (melting point 104-106° C.).

What is claimed is:

1. A process for preparing a carboxamide of formula (I)

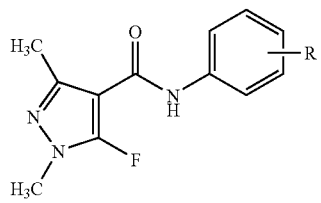

(I)

in which

R is $C_3$-$C_{12}$-cycloalkyl, $C_3$-$C_{12}$-cycloalkenyl, $C_6$-$C_{12}$-bicycloalkyl, $C_2$-$C_{12}$-oxacycloalkyl, $C_4$-$C_{12}$-oxacycloalkenyl, $C_3$-$C_{12}$-thiacycloalkyl, $C_4$-$C_{12}$-thiacycloalkenyl, $C_2$-$C_{12}$-azacycloalkyl, each of which may optionally be mono- or polysubstituted identically or differently by $C_1$-$C_8$-alkyl, $C_1$-$C_8$-alkoxy, halogen and/or cyano, or phenyl which is optionally mono- to pentasubstituted identically or differently, where the substituents are each selected from the list $W^1$, or unsubstituted $C_2$-$C_{20}$-alkyl, or $C_1$-$C_{20}$-alkyl which is mono- or polysubstituted identically or differently by halogen, $C_1$-$C_6$-alkylthio, $C_1$-$C_6$-alkylsulfinyl, $C_1$-$C_6$-alkylsulfonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkyl-sulfinyl, $C_1$-$C_6$-haloalkylsulfonyl, $C_1$-$C_6$-haloalkoxy, $C_1$-$C_6$-haloalkylamino, halo-di ($C_1$-$C_6$-alkyl)amino, -Si$R^1R^2R^3$ and/or $C_3$-$C_6$-cycloalkyl, where the cycloalkyl moiety may in turn optionally be mono- to tetrasubstituted identically or differently by halogen, $C_1$-$C_{20}$-alkyl and/or $C_1$-$C_4$-haloalkyl, $W_1$ is halogen, cyano, nitro, amino, hydroxyl, $C_1$-$C_8$-alkyl, $C_1$-$C_8$-alkoxy, $C_1$-$C_8$-alkyl-thio, $C_1$-$C_8$-alkylsulfinyl, $C_1$-$C_8$-alkylsulfonyl, $C_2$-$C_6$-alkenyl, $C_2$-$C_6$-alkenyloxy; $C_1$-$C_6$-haloalkyl, $C_1$-$C_6$-haloalkoxy, $C_1$-$C_6$-haloalkylthio, $C_1$-$C_6$-haloalkylsulfinyl or $C_1$-$C_6$-haloalkylsulfonyl having in each case from 1 to 13 identical or different halogen atoms; $C_2$-$C_6$-haloalkenyl or $C_2$-$C_6$-haloalkenyloxy having in each case from 1 to 11 identical or different halogen atoms; $C_3$-$C_6$-cycloalkyl or $C_3$-$C_6$-cyclo-alkyloxy;

$R^1$ and $R^2$ are each independently hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, $R^3$ is hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkyl-thio-$C_1$-$C_4$-alkyl, $C_2$-$C_8$-alkenyl, $C_2$-$C_8$-alkynyl, $C_1$-$C_6$-haloalkyl, $C_2$-$C_6$-halo-alkenyl, $C_2$-$C_6$-haloalkynyl, $C_3$-$C_6$-cycloalkyl, or in each case optionally substituted phenol or phenylalkyl, said process comprising reacting 5-fluoro- 1,3-dimethyl-1H-pyrazole-4-carbonyl fluoride of formula (II)

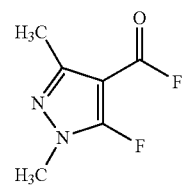

(II)

with aniline derivatives of formula (III)

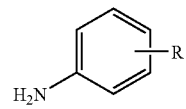

(III)

in which R is as defined above, in the presence of an acid acceptor of formula (IV)

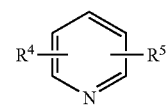

(IV)

in which $R^4$ and $R^5$ are each independently $C_1$-$C_3$-alkyl.

2. The process as claimed in claim 1, wherein the acid acceptor used is 2-methylpyridine, 2,3-dimethylpyridine, 2-methyl-5-ethylpyridine, 2,6-dimethylpyridine, 2,4-dimethylpyridine, 3,4-dimethylpyridine, and/or 2,4,6-trimethylpyridine.

3. The process as claimed in claim 1, wherein a temperature of from 100 to 150° C. is employed.

4. The process as claimed in claim 1, wherein an aniline derivative of formula (III-1)

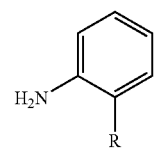

(III-1)

is used.

5. The process as claimed in claim 1, wherein 2-(1,3-dimethylbutyl)-phenylamine is used as the aniline derivative of the formula (III).

6. The process as claimed in claim 2, wherein a temperature of from 100 to 150° C. is employed.

7. The process as claimed in claim 2, wherein an aniline derivative of formula (III-1)

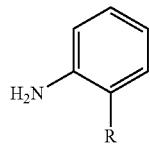

(III-1)

is used.

8. The process as claimed in claim 3, wherein an aniline derivative of formula (III-1)

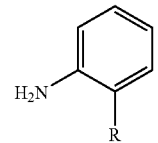

(III-1)

is used.

9. The process as claimed in claim 2, wherein 2-(1,3-dimethylbutyl)-phenylamine is used as the aniline derivative of the formula (III).

10. The process as claimed in claim 3, wherein 2-(1,3-dimethylbutyl)-phenylamine is used as the aniline derivative of the formula (III).

11. The process as claimed in claim 4, wherein 2-(1,3-dimethylbutyl)-phenylamine is used as the aniline derivative of the formula (III).

* * * * *